United States Patent [19]

Cronenberg et al.

[11] Patent Number: 4,615,340
[45] Date of Patent: Oct. 7, 1986

[54] SENSOR ASSEMBLY SUITABLE FOR BLOOD GAS ANALYSIS AND THE LIKE AND THE METHOD OF USE

[75] Inventors: Richard A. Cronenberg, Mahwah, N.J.; Stephen I. Shapiro, Scarsdale, N.Y.

[73] Assignee: Becton, Dickinson and Company, Franklin Lakes, N.J.

[21] Appl. No.: 822,963

[22] Filed: Jan. 28, 1986

Related U.S. Application Data

[63] Continuation of Ser. No. 706,051, Feb. 27, 1985, which is a continuation-in-part of Ser. No. 455,092, Jan. 3, 1983, abandoned.

[51] Int. Cl.$^4$ .................................................. A61B 5/05
[52] U.S. Cl. ..................................... 128/635; 128/765; 204/415
[58] Field of Search .................. 128/632, 635, 765; 204/415

[56] References Cited

U.S. PATENT DOCUMENTS

| | | | |
|---|---|---|---|
| 3,726,777 | 4/1973 | Macur | 204/403 |
| 3,795,239 | 3/1974 | Eberhard et al. | 128/635 |
| 3,838,682 | 10/1974 | Clark et al. | 128/635 |
| 3,957,613 | 5/1976 | Macur | 128/635 |
| 3,997,420 | 12/1976 | Buzza | 204/415 |
| 4,005,700 | 2/1977 | Parker | 128/632 |
| 4,062,750 | 12/1977 | Butler | 204/415 |
| 4,197,852 | 4/1980 | Schindler et al. | 128/635 |
| 4,197,853 | 4/1980 | Parker | 128/635 |
| 4,230,537 | 10/1980 | Delante et al. | 204/415 |
| 4,327,745 | 5/1982 | Ford, Jr. | 128/765 |
| 4,338,174 | 7/1982 | Tamura | 204/415 |
| 4,401,547 | 8/1983 | Schinkmann et al. | 204/415 |
| 4,535,786 | 8/1985 | Kater | 128/630 |

FOREIGN PATENT DOCUMENTS

| | | | |
|---|---|---|---|
| 0009129 | 4/1980 | European Pat. Off. | 128/635 |
| 2025065 | 1/1980 | United Kingdom | 128/635 |

OTHER PUBLICATIONS

Gotoh et al, "Continuous Recording of Human Cerebral Blood Flow and Metabolism: Methods for Electronic Monitoring of Arterial and Venous Gases and Electrolytes", Medical Research Engineering, Second Quarter, 1966, pp. 13–19.

Primary Examiner—Kyle L. Howell
Assistant Examiner—Ruth S. Smith
Attorney, Agent, or Firm—Richard J. Rodrick

[57] ABSTRACT

A sensor assembly for electrochemical analysis of a substance comprises a housing and electrodes for sensing selective gases and ions within the housing. A sampler is associated with the housing for introducing the substance to be analyzed into the housing and for allowing the selective gas and ion content thereof to be sensed without physical contact with the gas and ion sensing electrodes. A method of detecting gases and ions in a substance comprises withdrawing a quantity of a substance from a source and directly contacting the substance with a gas and ion permeable medium as it is withdrawn from the source. Gases and ions are caused to permeate through the medium whereupon the gases and ions are detected by a sensing mechanism.

27 Claims, 5 Drawing Figures

SENSOR ASSEMBLY SUITABLE FOR BLOOD GAS ANALYSIS AND THE LIKE AND THE METHOD OF USE

This application is a continuation of application Ser. No. 706,051, filed Feb. 27, 1985, which is a continuation-in-part of application Ser. No. 455,092, filed 1-3-83, now abandoned.

BACKGROUND OF THE INVENTION

1. Field of the Invention

The present invention relates to a sensor assembly for electrochemical analysis of a substance, its method of use and its major constituative components, and more particularly, concerns a sensor assembly for blood gas analysis at the bedside of a patient, its method of use and major constituative components.

2. Description of the Prior Art

Blood gas analysis has been performed on arterial blood of patients, particularly those with a critical illness, to determine the acid base and blood gas condition of these patients in assessing overall homeostasis. In particular, arterial pH, $pO_2$ and $pCO_2$ are measured from a sample of arterial blood to determine the biochemical status of the patient's blood. In accordance with conventional techniques for arterial blood gas analysis, the therapist responsible for obtaining the sample generally starts the procedure with an arterial blood gas kit dispensed from a central location (nursing station or lab). This blood gas kit is then brought to the bedside of the patient and opened. A bag is normally provided within each kit for ice, or a suitable container may be used. The bag or container is filled with a slurry of crushed ice and water and brought to the patient's room. A syringe is taken from the arterial blood gas kit and appropriately labeled according to standard practice. The inside of the syringe is normally coated with heparin at bedside, and excess heparin is expelled from the syringe by pushing the plunger inwardly until it stops. A small amount of heparin usually remains within the syringe which prevents the blood sample from clotting.

At this time, the therapist locates the patient's artery, preps the site with alcohol or the like and inserts the syringe needle into the artery. Arterial pressure forces blood into the syringe until it is filled to the desired level whereupon the therapist removes the needle from the patient and suitably caps it. The patient now requires pressure held on the site of the artery for a period of about five minutes until the bleeding stops. Air remaining in the syringe is removed, and the syringe is normally rolled between the therapist's hands to assure a complete mixing of the heparin, whereupon the filled syringe is placed in the container of ice. From the patient's bedside, the sample of blood is transported to the laboratory where it is analyzed.

In the laboratory, the sample is taken to the blood gas analyzer, rolled between the therapist's hands again to be sure it is thoroughly mixed, and injected into the analyzer. After a period of one to two minutes, the analysis is completed and either transcribed in writing by the operator of the analyzer or printed thereby. The results of this analysis are then brought back for listing on the patient's bedside chart. In addition, the patient's doctor is normally notified of these results. In normal, conventional blood gas analyses as described above, the average time from syringe preparation to the printout of the final results is about twenty minutes. Moreover, it has been estimated that as much as thirty percent (30%) to fifty percent (50%) of a respiratory therapy department's staffing may be involved in arterial blood gas procedures.

It can be seen that improvements in time and personpower in arterial blood gas analysis are desirable. Transportation of the arterial blood gas sample to a remote, central lab not only takes time, but could introduce errors or inaccuracies in the final analysis if the sample has not been treated properly. Furthermore, inasmuch as the blood gas sample must literally be transferred into the central processing unit from the original arterial syringe, the entire procedure is subjected to even more inaccuracies or opportunities for error.

As is evident from the above description, it would be most desirable to be able to perform the arterial blood gas analysis at the patient's bedside, i.e., the measurements of blood pH, $pO_2$ and $pCO_2$, and perhaps other blood information, would be available to the therapist immediately without having to transport the sample to a remote, central laboratory. One of the problems associated with such a proposed bedside technique, of course, involves equipment expense and perhaps a multiplicity of units which may not read uniformly. However, state of the art technology and carefully prepared calibration techniques are available to minimize equipment expense and assure that bedside blood gas analysis equipment will make substantially uniform and reproducible measurements. Another problem for such a proposed bedside technique involves the sensing devices to sense pH, $pO_2$ and $pCO_2$. A viable technique has been heretofore unknown which would allow the electrochemical analysis of blood pH, $pO_2$ and $pCO_2$ in a portable sensing device wherein the electrodes do not have to be cleaned after each use, which is normally performed on the electrodes of centrally located blood gas analyzers. While transcutaneous electrodes are known and available for measuring certain blood gases, it is believed that such transcutaneous electrodes do not measure the transfer of ions thereacross which would be necessary in measuring pH values. A sensor for electrochemical analysis has recently been described in U.S. Pat. No. 4,197,582, which is described as capable of measuring blood gases and ions. However, the sensor of the aforementioned patent is intended for in vivo measurements in a precisely predeterminable location in the living body.

Therefore, the present invention is directed to overcoming the problematical areas set forth above while at the same time achieving the desirable aims of a bedside or portable blood gas analyzer and procedure.

SUMMARY OF THE INVENTION

The sensor assembly for electrochemical analysis of a substance in accordance with the present invention comprises a housing and means for sensing selective gases and ions within the housing. The assembly includes means for introducing the substance to be analyzed into the housing and for allowing the selective gas and ion content thereof to be sensed without physical contact with the gas and ion sensing means.

In a preferred embodiment of this aspect of the invention, the housing has an open end and electrodes for sensing oxygen, carbon dioxide and hydrogen ions (pH) are located inside the housing and spaced from the open end by a recess. A gas-permeable, ion-impermeable membrane covers the oxygen and carbon dioxide electrodes substantially at the interface with the recess. Means connects the electrodes into an electrical circuit to measure values of $pO_2$, $pCO_2$ and pH sensed by the respective electrodes. A blood sampler has a cavity covered by a gas and ion permeable membrane, a port communicating with the cavity for entry of blood therein and a vent port communicating with the cavity and adapted to allow air to pass out of the cavity, but not blood. The sampler is removably positioned in the recess of the housing so that the membranes are in substantially face-to-face engagement and the ion electrode is in contact with the gas and ion permeable membrane of the sampler.

In another aspect of the present invention, a sensor for electrochemical analysis of a substance comprises a housing and means for sensing selective gases and ions within the housing. Gas-permeable, ion-impermeable means covers the selective gas sensing means, but not the selective ion sensing means. Means connects the gas and ion sensing means into an electrical circuit to measure the values sensed thereby.

In a further aspect of the present invention, a device for providing a sample of a liquid or solid substance for electrochemical analysis comprises a body member having a cavity therein. Means is provided for placing a substance into the cavity and for purging air from the cavity after the substance is placed therein. This device further includes means for passing selective gases and ions out of the cavity without removing the substance therefrom.

In another aspect of the present invention, a method of detecting gases and ions in a substance comprises withdrawing a quantity of a substance from a source, and directly contacting the substance with a gas and ion permeable medium as it is withdrawn from the source. Gases and ions are caused to permeate through the medium and are detected by sensing means.

In a preferred embodiment of this method aspect of the present invention, the method simultaneously measures the partial pressures of oxygen and carbon dioxide and the pH level of arterial blood of a patient at bedside. This preferred method includes placing a blood sampler having a gas and ion permeable membrane into close proximity to measuring electrodes sensitive to oxygen, carbon dioxide and hydrogen ions (pH). A needle is inserted into an artery of a patient and blood is withdrawn from the artery directly into the sampler at the bedside of the patient. Oxygen and carbon dioxide and hydrogen ions are caused to permeate through the membrane and be sensed by the electrodes. This method further includes displaying the sensed values of $pO_2$, $pCO_2$ and pH related to the arterial blood. The sampler is then removed from its position adjacent the electrodes after the values are sensed.

In accordance with the principles of the present invention, the most notable objective which the present invention achieves is the ability to measure and display (if desired) selective parameters of arterial blood at the bedside of a patient from whom the sample of blood has been taken. Most advantageously, the present invention eliminates the need to have the blood sample transported to a central lab for analysis, while further eliminating the need to transfer the sample from the original blood gas syringe into a blood gas analyzer at the central location. Accordingly, significant time and effort of the respiratory therapist are saved by utilization of the present invention and blood gas analysis technique. Furthermore, the present invention provides information about selective blood gases and ions without relying upon contact between the blood and the sensing electrodes, as is now performed in the known and available blood gas analyzers. Thus, electrode cleaning has also been obviated by the present invention. It is expected that the blood gas analyzer of the present invention can be packaged so as to be hand-held or at least readily portable without the need for rolling carriers or the like. A significant feature of the present invention is the immediate analysis of arterial blood within seconds after it is withdrawn from the patient, thereby minimizing the environmental factors which may cause erroneous results in arterial blood taken from a patient. Particularly in the case of severely ill patients, the results of arterial blood gas analysis at bedside will allow the doctor to prescribe a course of action much quicker than the previous reliance on centrally located blood gas analysis. The benefits to the patient, in addition to the hospital and respiratory therapist staff, are clearly perceivable when the present invention is utilized for bedside blood gas analysis.

DETAILED DESCRIPTION

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Figure 1:
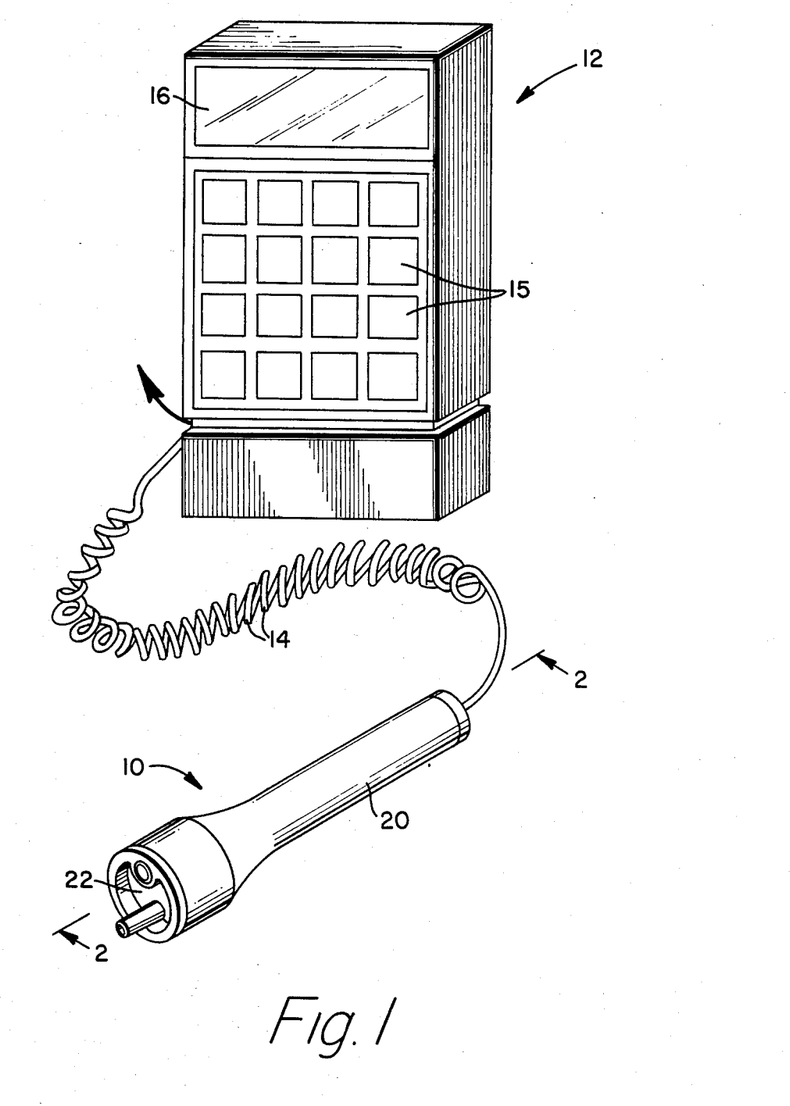
FIG. 1 is a perspective view of a preferred sensor assembly of the present invention suitable for blood gas analysis at the bedside of a patient, illustrated in conjunction with a representative device for providing blood gas information to the bedside clinician.

Adverting to the drawings, and FIG. 1, in particular, there is illustrated the preferred sensor assembly 10 in conjunction with a portable electrical blood gas analyzer 12. An appropriate electrical cord 14 interconnects sensor assembly 10 and analyzer 12. While the internal components of analyzer 12 will not be described here, suffice it to say that the analyzer includes state of the art technology for receiving a plurality of electrical signals from the sensor assembly and performing a number of electrical operations before displaying information to the user with respect to those signals. For example, patient data, such as patient identification, accession number, patient temperature and $FIO_2$ (Fractional Inspired Oxygen concentration), may be fed into the analyzer by virtue of one or more of the keys 15 thereon.

The analyzer is programmed to collate the electrical signals from the sensor assembly and store the measured values of $pO_2$, $pCO_2$ and pH relating to the blood sample being analyzed. These values, and others, if desired, may be displayed on screen 16 of the analyzer either automatically or upon command of the user. Further, the measured blood values may be stored in the analyzer for later recall. It is anticipated that analyzer 12 would have an interface capability with a base unit for calibration and patient data retrieval.

Figure 2:
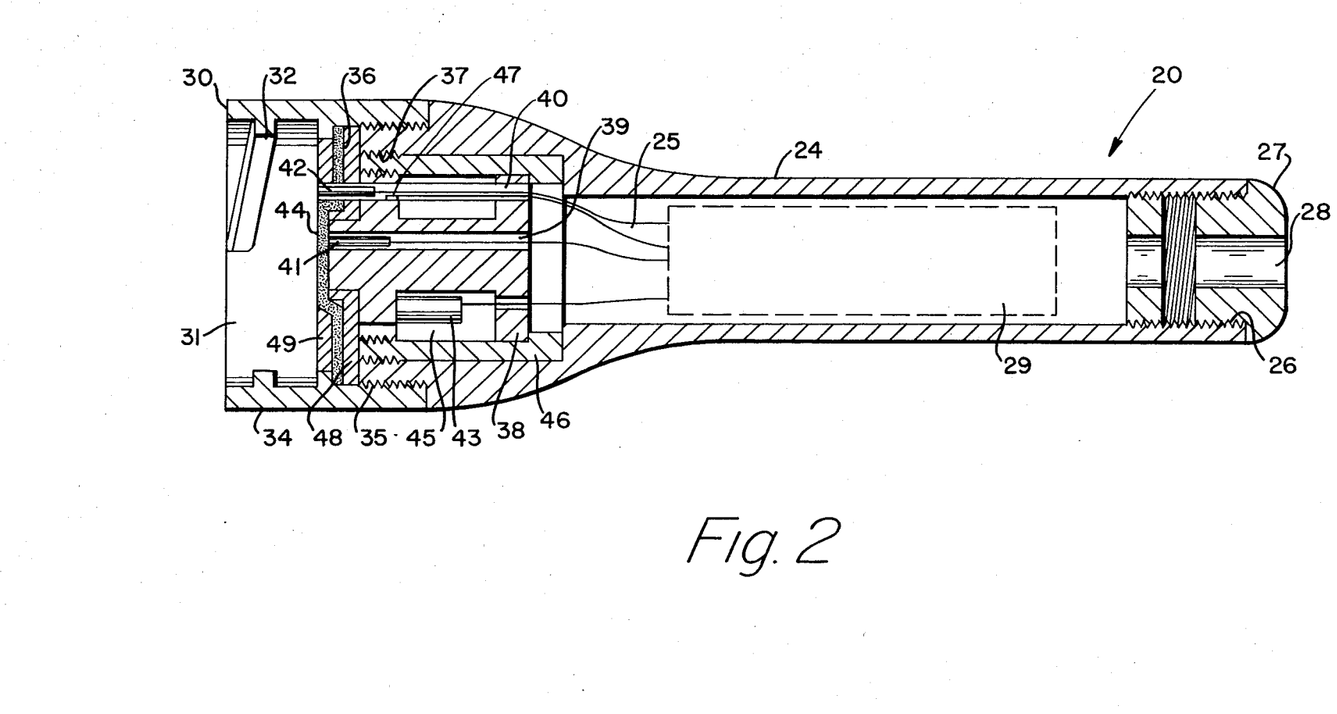
FIG. 2 is an enlarged cross-sectional view of the sensor element of the assembly of FIG. 1 taken along line 2—2 thereof illustrated without the blood sampler in position.

Sensor assembly 10 is comprised of two major components, a sensor 20 and a removable, preferably disposable, blood sampler 22. Referring to FIG. 2, the details of sensor 20 are more clearly illustrated. This sensor includes a housing 24 which is essentially wand-like and preferably sized to be gripped by the hand of the user. Housing 24 includes a hollow cavity 25 preferably extending completely through the housing. A first or proximal open end 26 of the housing is normally closed with a threaded plug 27 having an opening 28 therethrough for the passage of electrical leads (not shown) as part of electrical cord 14 illustrated in FIG. 1. Included in the central area of cavity 25 are the electronics 29 which interface with the electrode signals, described hereinafter, and which pass electrical information to the analyzer. The distal or second end 30 of housing 24 preferably has an enlarged diameter with respect to the remainder of the housing, so as to preferably appear somewhat bulbus. Just inside end 30 is a recess 31 which includes an internal thread 32 which should provide at least a one-quarter turn for engagement with a blood sampler, as described more fully hereinafter. It is preferred that the distal end 30, recess 31 and thread 32 be part of a removable distal segment 34 which is threaded onto the housing by mating threads 35. A shoulder 36 is provided on the distal segment of the housing to assist in securing the internal components of the sensor.

Positioned inside the bulbus end of the housing and secured thereto by mating threads 37 is an inner body 38. This inner body is preferably a self-contained sub-assembly which is spaced from distal end 30 by virtue of recess 31. Included in inner body 38 are two narrow passageways 39 and 40 extending completely therethrough. Placed inside passageway 39 are three electrodes 41: one for sensing oxygen, one for sensing carbon dioxide and a common cathode electrode associated with the oxygen and carbon dioxide electrodes which serve as anodes. These electrodes are well-known in the art and may be selected for the specific gases which are to be monitored and analyzed. It is also preferred that electrodes 40 within passageway 39 be immersed in an electrolyte solution, and covered by a gas-permeable, ion-impermeable membrane 44. Membrane 44 is chosen to allow selective gases, such as oxygen and carbon dioxide, to diffuse therethrough while preventing other gases and ions from passing therethrough. As can be seen in FIG. 2, membrane 44 faces recess 31. A number of materials may be utilized for the gas-permeable, ion-impermeable membrane, but the materials of choice are polytetrafluoroethylene or polypropylene.

Positioned in passageway 40 are two electrodes 42, one being a pH electrode and the other a pH reference electrode. The pH electrode is located in passageway 40 so that it is immediately adjacent recess 31 and so that it can be contacted by the blood sampler when positioned in the recess. Once again, electrodes for measuring pH and to serve as a pH reference electrode are known and may be appropriately selected for the specific function in the present invention. It is preferred that a thermistor 47 be included within passageway 40 so that the temperature of this end of the housing, including the sample of blood being analyzed, may be measured. In addition, and in order to effectively control blood sample temperature in conjunction with the functions of the thermistor, an area 45 is provided in the inner body into which an electrical heater 43 is positioned. A preferably plastic insulator 46 forms the outside surface of the inner body and serves as an electrical insulator as well as a heat insulator particularly when heater 43 is operating.

Inasmuch as membrane 44 should be replaced periodically for most effective operation, inner body 38 also includes a pair of washers 48 and 49. The peripheral surfaces of membrane 44 are sandwiched between the washers which can be dissembled so that the membrane can be removed and subsequently replaced. In assembling the components of the sensor, the elements of the inner body are normally assembled first, outside of the housing. Distal segment 34 has been removed from the bulbus part of the housing. The completed inner body sub-assembly is then appropriately wired or electrically connected to the electronics inside the housing; the inner body sub-assembly is then positioned inside the bulbus end of the housing. Distal segment 34 is then threaded onto the housing so that shoulder 36 engages washer 48 thereby securing the inner body within the housing. When membrane 44 needs replacement, the above assembly steps are reversed.

Figure 3:
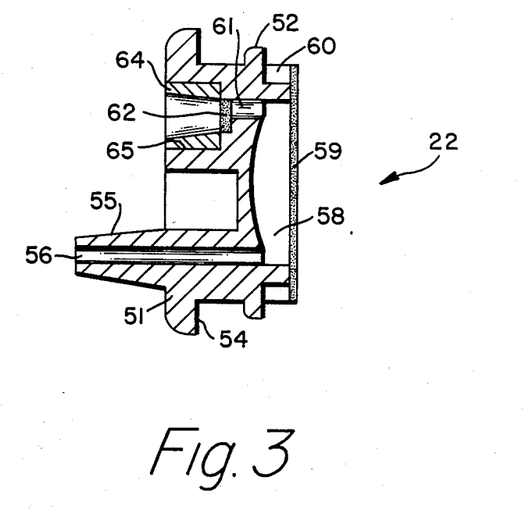
FIG. 3 is an enlarged cross-sectional view of the preferred configuration of the removable blood sampler of the present invention illustrated unconnected to the sensor assembly.
Figure 4:
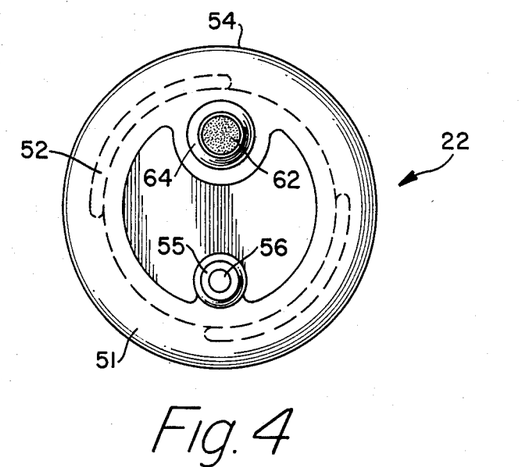
FIG. 4 is an enlarged front elevational view of the blood sampler of FIG. 3.

Turning now to FIGS. 3 and 4, the details of blood sampler 22 are more clearly illustrated. This blood sampler is comprised of a body member 51 which is preferably sized to fit within recess 31 of the above-described sensor. The outside periphery of the body includes a thread 52, such as a quarter-turn thread, for engagement with internal thread 32 inside the recess of the sensor. A flange 54 is preferably included so as to abut against the end of the housing of the sensor when the blood sampler is connected thereto. Extending outwardly from body 51 is preferably a tapered extension 55 which is adapted to receive the hub of a needle for the withdrawal of blood from the patient. Extending through the tapered extension and the body is a blood entry port 56. This entry port communicates with a cavity 58 on the side of the blood sampler which is intended to face the inner body of the sensor as described above. Covering cavity 58 is a gas and ion permeable membrane 59, which may be specifically selected to allow oxygen, carbon dioxide and hydrogen ions to pass therethrough. Membrane 59, however, is adapted to prevent blood from passing therethrough so that the blood sample taken from the patient remains inside the sampler during the blood gas analysis procedure. The peripheral surfaces of membrane 59 are preferably sandwiched between body 51 and a retaining ring 60 for purposes of assembly. It is understood that the gas and ion permeable membrane may be affixed to the blood sampler by other convenient means. Desirable materials for the gas and ion permeable membrane include polycarbonate and cellulosic materials, with the material of choice being Cuprophan TM cellulose.

Also communicating with cavity 58 is a vent port 61. This vent port facilitates the removal of air from the cavity when blood from the entry port is filling the cavity. In order to assure that no blood escapes from the cavity, an air permeable, liquid impermeable membrane 62 extends across vent port 61. It is preferred that membrane 62 be included in a plug 64 which can be readily inserted into a recess 65 formed in body 51 adjacent vent port 61.

Inasmuch as the blood sampler is intended to be disposable after it is removed from the sensor assembly following blood gas analysis, it is preferred that the components of the blood sampler, except for the aforementioned membranes, be made of plastic.

Figure 5:
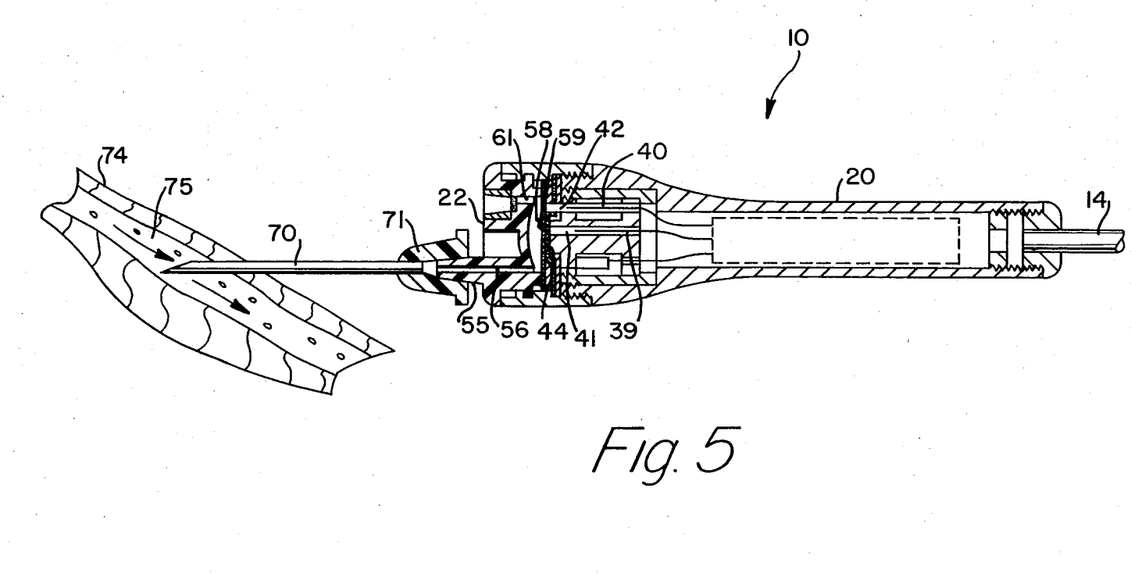
FIG. 5 is a cross-sectional view of the preferred sensor assembly as it appears during the withdrawal of arterial blood from a patient and the initial stages of blood gas analysis at the bedside of a patient.

Turning now to FIG. 5, taken in conjunction with FIGS. 2-4, sensor assembly 10 is illustrated as it would appear during use. Prior to actual withdrawal of blood from the patient, sensor assembly 10 and analyzer 12 are brought to the bedside of the patient. Appropriate information with respect to the patient is entered into the analyzer, as described above. A disposable blood sampler 22 is then inserted into the recess of the sensor so that membrane 59 of the sampler and gas-permeable, ion-impermeable membrane 44 of the sensor are in face-to-face engagement, with the pH electrode 41 in passageway 40 being in substantial contact with membrane 59 of the blood sampler. A conventional needle 70 by virtue of its hub 71, is connected to tapered extension 55 of the blood sampler. A patient 74 is then prepared in the customary manner for the withdrawal of arterial blood.

As can be seen in FIG. 5, the point of the needle has entered an artery 75 whereupon arterial blood is forced by arterial pressure, through the needle and entry port 56 for ultimate delivery to cavity 58. The sensor assembly 10 is normally hand-held while arterial blood is being withdrawn from the patient. As blood enters cavity 58, any air previously therein will be expelled through air vent 61 which also prevents the escape of blood from the cavity, as described above. As soon as blood starts filling cavity 58, oxygen, carbon dioxide and hydrogen ions start diffusing through membrane 59. The pH electrode inside the sensor immediately senses hydrogen ions and sends an electrical signal to the analyzer for measurement of the blood pH value. At the same time, oxygen and carbon dioxide pass through gas permeable membrane 44 within the sensor and are sensed by the oxygen and carbon dioxide electrodes. Once again, electrical signals representative of the values of oxygen and carbon dioxide are fed to the analyzer. As can be seen in FIG. 5, gas and ion sensing is conducted in an in vitro environment, i.e., outside the body after blood has been collected in cavity 58 of the blood sampler. Further, the sensing starts immediately, even while the needle is still inserted in the patient. During this procedure, values of $pO_2$, $pCO_2$ and pH may be digitally displayed on screen 16 of analyzer 12, as previously described in conjunction with FIG. 1. The needle need not remain in the artery of the patient during the analysis period, but may be removed from the patient's artery as soon as the blood sampler has been filled. After the needle has been removed from the patient, pressure is held on the artery, in conventional fashion for a period of about five minutes until the bleeding stops.

It is expected that the entire blood analysis can be completed by virtue of the present invention and bedside analyzer within a period of about two minutes from the time when the arterial blood is taken from the patient. Accordingly, the measured blood values can be obtained and displayed to the bedside therapist during the normal time it takes to apply pressure to the patient's artery after the needle has been withdrawn. After the analysis has been completed, the needle is discarded and the blood sampler is removed from the distal end of the housing. The sensor is then immediately ready for another arterial sample without the necessity for cleaning electrodes or immediate re-calibration. As alluded to above, the blood gas analyzer may require periodic re-calibration, but it need not be performed at bedside and more than likely, re-calibration of the analyzer might be appropriate once per hospital shift.

Thus, the present invention provides a sensor assembly suitable for blood gas analysis and the like at the bedside of a patient. The time for determination of arterial blood gas values is significantly reduced when using the present invention as well as the elimination or reduction of inaccuracies which might be attendant with the presently available blood gas analysis procedure which relies upon analysis at a central laboratory.

What is claimed is:

1. A hand-holdable sensor assembly suitable for use in a device for blood gas analysis and the like at the bedside of a patient comprising:
    a portable housing sized to be held by the hand of a user having an open end;
    electrode means, including electrodes for sensing oxygen, carbon dioxide and hydrogen ions located inside said housing and spaced from said open end by a recess;
    a gas-permeable, ion-impermeable membrane positioned within said recess and covering said oxygen and carbon dioxide electrodes;
    means for connecting said electrodes into an electrical circuit which includes means for measuring and displaying values of $pO_2$, $pCO_2$ and pH sensed by the respective electrodes; and
    a blood sampler having a cavity covered by a gas and ion-permeable membrane, a port communicating with said cavity for the entry of blood therein, said port adapted for connection to a needle for penetrating a blood vessel of the patient, and a vent port communicating with said cavity, said vent port including means for allowing air to pass out of said cavity, but not blood, said sampler being removably positioned in said recess so that said membranes are in substantially face-to-face engagement and said ion electrode is in contact with said gas and ion-permeable membrane of said sampler.

2. The assembly of claim 1 wherein said oxygen and carbon dioxide electrodes are measuring anodes and said assembly further includes a common electrode serving as a cathode associated with said anodes.

3. The assembly of claim 2 wherein said oxygen, carbon dioxide and common electrodes are contained within an inner body positioned inside said housing and are immersed in an electrolyte medium and covered by said gas-permeable, ion-impermeable membrane.

4. The assembly of claim 1 wherein said gas-permeable, ion-impermeable membrane is removable from said assembly.

5. The assembly of claim 1 which further includes another electrode serving as a hydrogen ion reference electrode during the measurement of pH values.

6. The assembly of claim 1 which further includes a heater located near said recess for heating the housing area around said electrodes and the recess into which said blood sampler is positioned.

7. The assembly of claim 6 which further includes a sensing element for measuring the temperature to which said housing area is heated.

8. The assembly of claim 1 wherein said gas-permeable, ion-impermeable membrane is made of polytetrafluorethylene and said gas and ion permeable membrane is made of cellulosic material.

9. The assembly of claim 1 wherein said means for connecting includes an electrical line having a sufficient number of electrical conduits to carry a plurality of signals from said housing to the electrical circuit for measuring and displaying said values.

10. The assembly of claim 1 wherein the entry port of said sampler includes a tapered extension therearound onto which a hub of a needle is adapted to be connected.

11. The assembly of claim 1 wherein said vent port means of said sampler includes an air-permeable, liquid-impermeable membrane thereacross.

12. A hand-holdable sensor assembly for use in a device for blood gas analysis at the bedside of a patient comprising:
   a wand-like, portable housing sized to be held by the hand of a user and having an open end;
   an inner body positioned inside said housing and spaced from said open end by a recess, said body containing oxygen and carbon dioxide measuring electrodes and a common reference electrode associated with said measuring electrodes, all of said electrodes immersed in an electrolyte medium, said inner body being covered by a gas-permeable, ion-impermeable membrane facing said recess;
   pH and pH reference electrodes in said housing located near said recess;
   electrical lead wires attached to said electrodes for connecting same into an electrical circuit which includes means for measuring and displaying values of oxygen, carbon dioxide and pH sensed by the respective electrodes; and
   a blood sampler having a cavity covered by a gas and ion permeable membrane, a port communicating with said cavity for the entry of blood therein, said port adapted for connection to a needle for penetrating a blood vessel of the patient, a vent port communicating with said cavity including an air-permeable, liquid-impermeable membrane thereacross adapted to allow air to pass out of said cavity but not blood, said sampler being removably positioned in said recess so that said membranes are in face-to-face engagement and said pH electrode is in contact with said gas and ion permeable membrane of said sampler.

13. A hand-holdable sensor for use in a device for blood gas analysis and the like at the bedside of a patient comprising:
   a portable housing sized to be held by the hand of a user having an open end;
   electrode means, includng electrodes, for sensing oxygen, carbon dioxide and hydrogen ions located inside said housing and spaced from said open end by a recess;
   a gas-permeable, ion-permeable membrane positioned within said recess and covering only said oxygen and carbon dioxide electrodes; and
   means for connecting said electrodes into an electrical circuit to measure values of $pO_2$, $pCO_2$ and pH sensed by the respective electrodes.

14. A method of measuring the partial pressures of oxygen and carbon dioxide and the pH level of arterial blood of a patient at bedside comprising:
   withdrawing blood from an artery of a patient;
   directing said blood as it is withdrawn into in vitro contact with a gas and ion-permeable membrane located at the bedside of a patient;
   causing oxygen, carbon dioxide and hydrogen ions to permeate through said membrane and be sensed by measuring electrodes located at the bedside of the patient; and
   providing information at bedside relating to measured values of the partial pressures of arterial oxygen and carbon dioxide and pH.

15. The method of claim 14 wherein said withdrawing step includes filling a blood sampler with a quantity of arterial blood, said sampler including said gas and ion-permeable membrane.

16. The method of claim 15 wherein said directing step includes placing said sampler so that said membrane is adjacent said measuring electrodes.

17. The method of claim 16 which further includes removing said sampler from its position adjacent said electrodes after said information is provided.

18. The method of claim 14 wherein said withdrawing step includes inserting a needle into an artery of the patient.

19. The method of claim 18 wherein oxygen, carbon dioxide and hydrogen ions are sensed by said measuring electrodes while said needle is still inserted in the patient.

20. The method of claim 14 wherein said providing step includes displaying the values of $pO_2$, $pCO_3$ and pH.

21. The method of claim 20 wherein said values are displayed digitally.

22. The method of claim 14 wherein said directing step includes holding a housing containing said electrodes in the hand of the user and connecting said housing into fluid communication with an artery of the patient so that arterial blood flows toward said housing.

23. A method of detecting gases and ions in blood comprising:
   withdrawing blood from a living source;
   directly contacting said blood with a gas and ion-permeable medium as it is being withdrawn;
   causing gases and ions to permeate through said medium; and
   detecting said gases and ions by sensing means.

24. The method of claim 23 wherein said detecting step includes providing information relating to measured values of the gases and ions detected.

25. The method of claim 23 wherein said detecting step includes detecting only pre-selected gases and ions in the blood.

26. A method of measuring the partial pressures of oxygen and carbon dioxide and the pH level of arterial blood of a patient at bedside comprising:
   placing a blood sampler having a gas and ion-permeable membrane into close proximity to measuring electrodes sensitive to oxygen, carbon dioxide and hydrogen ions;
   inserting a needle into an artery of a patient;
   withdrawing blood from said artery directly into said sampler at the bedside of the patient;
   causing oxygen, carbon dioxide and hydrogen ions to permeate through said membrane and be sensed by said electrodes;
   displaying the sensed values of $pO_2$, $pCO_2$ and pH related to said arterial blood; and
   removing said sampler from its position adjacent said electrodes after the values are sensed.

27. A method of detecting gases and ions in a substance comprising:

withdrawing a quantity of a substance from a source;

directly contacting said substance with a gas and ion-permeable medium as it is withdrawn from the source;

causing gases and ions to permeate through said medium; and detecting said gases and ions by sensing means.

* * * * *

UNITED STATES PATENT AND TRADEMARK OFFICE
CERTIFICATE OF CORRECTION

PATENT NO. : 4,615,340

DATED : October 7, 1986

INVENTOR(S) : Richard A. Cronenberg et al.

It is certified that error appears in the above-identified patent and that said Letters Patent is hereby corrected as shown below:

Column 9, line 59, "ion-permeable" should read
-- ion-impermeable --.

Signed and Sealed this

Twenty-third Day of December, 1986

Attest:

DONALD J. QUIGG

Attesting Officer     Commissioner of Patents and Trademarks